United States Patent [19]
Douglas et al.

[11] Patent Number: 6,066,647
[45] Date of Patent: May 23, 2000

[54] ZWITTERIONIC FORMS OF TROVAFLOXACIN

[75] Inventors: Allen J. M. Douglas; David B. Joseph, both of New London; Timothy Norris, Gales Ferry, all of Conn.

[73] Assignee: Pfizer Inc., New York, N.Y.

[21] Appl. No.: 09/011,725

[22] PCT Filed: Jul. 29, 1996

[86] PCT No.: PCT/IB96/00756

§ 371 Date: Jan. 29, 1998

§ 102(e) Date: Jan. 29, 1998

[87] PCT Pub. No.: WO97/07800

PCT Pub. Date: Mar. 6, 1997

[51] Int. Cl.[7] .................... A61K 31/4375; C07D 471/04
[52] U.S. Cl. ........................................... 514/300; 546/123
[58] Field of Search ............................... 514/300; 546/123

[56] References Cited

U.S. PATENT DOCUMENTS

| | | | |
|---|---|---|---|
| 4,234,578 | 11/1980 | Muller | 424/246 |
| 4,616,002 | 10/1986 | Kamber | 514/18 |
| 4,965,260 | 10/1990 | Lang | 514/192 |
| 5,164,402 | 11/1992 | Brighty | 514/300 |
| 5,206,256 | 4/1993 | Lang | 514/383 |
| 5,229,396 | 7/1993 | Brighty | 514/300 |

*Primary Examiner*—Evelyn Mei Huang
*Attorney, Agent, or Firm*—Peter C. Richardson; Paul H. Ginsburg; Bryan C. Zielinski

[57] ABSTRACT

The invention relates to a non-hygroscopic polymorph of the following compound

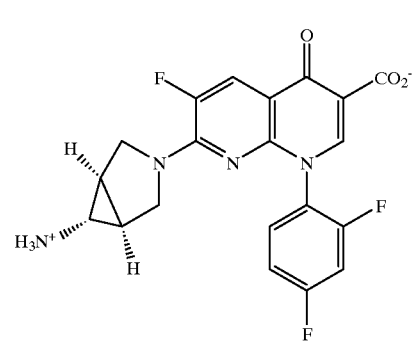

and to pharmaceutical compositions containing the above compound, methods of treating bacterial infections by administering the above compound, and to methods of preparing the above compound and related compounds.

8 Claims, No Drawings

ZWITTERIONIC FORMS OF TROVAFLOXACIN

This application is the national phase of PCT/IB 96/00756, filed on Jul. 29, 1996.

BACKGROUND OF THE INVENTION

This invention relates to the naphthyridone antibiotic trovafloxacin. More particularly, it relates to polymorphs and the pentahydrate of the zwitterionic form of thereof having the formula I, below, and methods for their preparation. The invention further relates to methods of using, and pharmaceutical compositions comprising, the compounds of the invention for treatment of bacterial infections in mammals. The antibacterial activity of the aforementioned naphthyridone antiliotic is described in U.S. Pat. Nos. 5,164,402 [the '402 patent] and 5,229,396 issued Nov. 17, 1992 and Jul. 20, 1993, respectively, the disclosures of which are hereby incorporated herein by reference in their entirety. The foregoing patents are assigned in common with the present application.

The zwitterionic forms of trovafloxacin are useful for the administration of the drug as a suspension.

SUMMARY OF THE INVENTION

According to a first embodiment of the invention there is provided a trovafloxacin zwitterionic crystal form having the formula

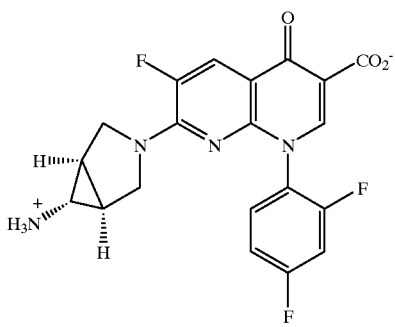

I which is selected from the group consisting of a) a non hygroscopic first polymorph PI exhibiting the following characteristic X-ray powder diffraction pattern

| Peak no. | 1 | 2 | 3 | 4 | 5 | 6 | 7 | 8 | 9 |
|---|---|---|---|---|---|---|---|---|---|
| 2_θ_(°) Cu | 6.9 | 9.8 | 11.3 | 12.0 | 13.9 | 16.1 | 16.6 | 17.1 | 17.4 |
| d space | 12.7 | 9.0 | 7.9 | 7.4 | 6.4 | 5.5 | 5.4 | 5.2 | 5.1 |

| Peak no. | 10 | 11 | 12 | 13 | 14 | 15 | 16 | 17 |
|---|---|---|---|---|---|---|---|---|
| 2_θ_(°) Cu | 19.7 | 22.9 | 23.6 | 24.9 | 25.4 | 25.9 | 27.7 | 29.5 |
| d space | 4.5 | 3.9 | 3.8 | 3.6 | 3.5 | 3.4 | 3.2 | 3.0 | b) a hygroscopic second polymorph PII exhibiting the characteristic X-ray powder diffraction pattern

| Peak no. | 1 | 2 | 3 | 4 | 5 | 6 | 7 | 8 |
|---|---|---|---|---|---|---|---|---|
| 2_θ_(°) Cu | 8.4 | 9.5 | 10.2 | 14.7 | 16.8 | 17.9 | 22.6 | 26.1 |
| d space | 10.6 | 9.3 | 8.7 | 6.0 | 5.3 | 5.0 | 3.9 | 3.4 | and c) a pentahydrate, trovafloxacin zwitterion pentahydrate, exhibiting the characteristic X-ray powder diffraction pattern

| Peak no. | 1 | 2 | 3 | 4 | 5 | 6 | 7 | 8 | 9 |
|---|---|---|---|---|---|---|---|---|---|
| 2_θ_(°) Cu | 6.6 | 8.6 | 12.7 | 13.3 | 15.9 | 18.6 | 19.2 | 20.1 | 21.0 |
| d space | 13.3 | 10.3 | 7.0 | 6.6 | 5.5 | 4.8 | 4.6 | 4.4 | 4.2 |

| Peak no. | 10 | 11 | 12 | 13 | 14 | 15 | 16 | 17 |
|---|---|---|---|---|---|---|---|---|
| 2_θ_(°) Cu | 22.5 | 22.9 | 23.6 | 24.9 | 25.4 | 25.9 | 27.7 | 29.5 |
| d space | 4.0 | 3.9 | 3.8 | 3.6 | 3.5 | 3.4 | 3.2 | 3.0 |

A second embodiment of the invention relates to a process for preparing a zwitterion, of trovafloxacin, of the formula I which is selected from the group consisting of a non hygroscopic polymorph PI, a hygroscopic polymorph PII and a pentahydrate thereof, as described above, comprising A. the steps of treating an aqueous suspension of a metastable form of the compound of the formula I 1) with a nonpolar solvent followed by azeotropic removal of residual water and vacuum drying to form said hygroscopic polymorph PII which exhibits the characteristic X-ray powder diffraction pattern described in claim 1;

2) with a polar solvent followed by azeotropic removal of residual water and vacuum drying; or 3) with water and air drying the residue at an elevated temperature, removing the mother liquor and air drying the residue at room temperature to constant weight to form the pentahydrate; or B) treating the hygroscopic second polymorph PII with a refluxing polar solvent to form the non-hygroscopic first polymorph PI.

According to a third embodiment of the invention there is provided a process for preparing the metastable form of the zwitterion, of trovafloxacin, of the formula I, by a) treating an acid salt of trovafloxacin with a base to raise the pH of the mixture to between 7.5 and 8.5 at an elevated temperature, removal of the mother liquor, washing the crystals with water and drying the crystals under vacuum at about 35 to about 40° C.; or b) treating a compound of the formula

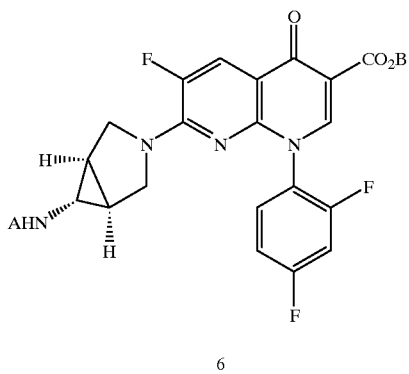

wherein A is hydrogen or an amine protecting group such as t-butyloxycarbonyl, benzyloxycarbonyl, $(C_1-C_6)$alkylcarbonyl and benzyl; and B is hydrogen or a carboxylic acid protecting group selected from benzyl, t-butyl and $(C_1-C_6)$alkyl; with an amine and/or carboxylic acid deprotecting agent, respectively.

A fourth embodiment of the invention provides a method of treating bacterial infections in a mammal which comprises administering to said mammal a bacterial infection treating effective amount of a compound of formula I as described above.

According to a fifth embodiment of the invention there is provided a composition for treating bacterial infections in a mammal which comprises a bacterial infection treating effective amount of a compound of formula I and a pharmaceutically acceptable carrier.

DETAILED DESCRIPTION OF THE INVENTION

The present invention relates to a compound comprising a stable zwitterionic form of the antibiotic trovafloxacin of the formula

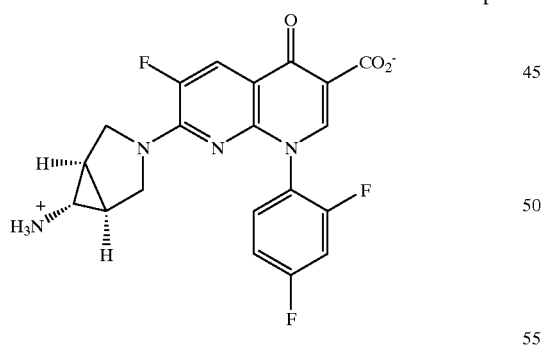

More particularly, it is related to a compound of the formula I which is selected from
  a) a non hygroscopic first polymorph PI exhibiting the characteristic X-ray powder diffraction pattern described above;
  b) a hygroscopic second polymorph PII exhibiting the characteristic X-ray powder diffraction pattern described above; and
  c) a pentahydrate, trovafloxacin zwitterion pentahydrate, exhibiting the characteristic X-ray powder diffraction pattern described above.

The invention also relates to processes for the preparation of the compounds of the formula I as illustrated in the following schemes.

SCHEME 1

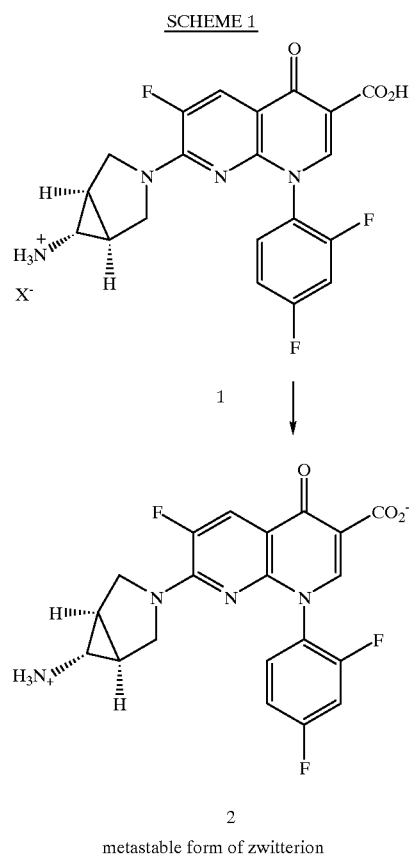

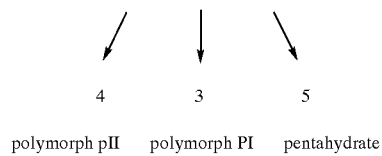

SCHEME 2

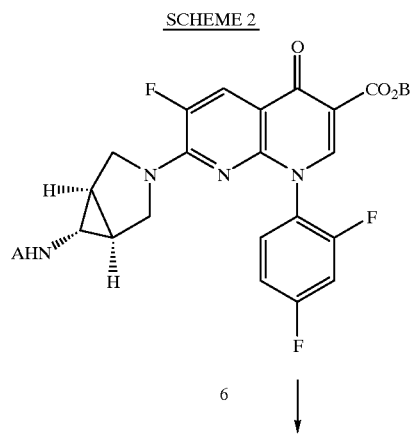

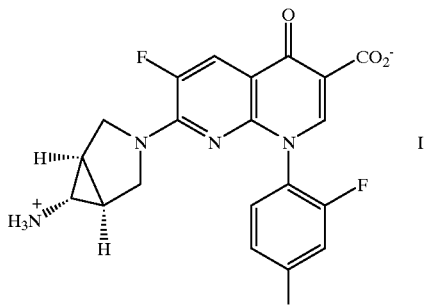

2 metastable forms of zwitterion

As shown in Scheme 1 a trovafloxacin salt 1, wherein X is an anion selected from those formed from mineral acids such as hydrochloric, sulfuric, nitric and phosphoric; organic acids such as sulfonic acids, e.g. benzenesulfonic (besylic), p-toluenesulfonic (PTSA, tosylic), methanesulfonic (MSA, mesylic) and trifluoromethanesulfonic (triflic); and carboxylic acids e.g., acetic, proprionic, benzoic, citric, tartaric, maleic, fumaric, succinic and malic, is converted to a metastable zwitterionic form 2 by raising the pH of a slurry comprising compound 1 to a pH of between about 7.5 and 8.5 at a temperature in the range of about 45 to about 55° C. using an aqueous basic solution. A preferred salt is the mesylate. The bases useful in the practice of this aspect of the invention include inorganic bases such as alkali or alkaline earth hydroxides, carbonates and bicarbonates and organic bases such as tri($C_1$–$C_6$)alkyl amines, pyridine and morpholine. A preferred aqueous base is saturated sodium bicarbonate. The wet product is then dried to constant weight, in vacuo, at a temperature from about 35 to about 40° C.

Alternatively, as shown in scheme 2, compound 2 may be prepared directly from protected precursors 6, of the trovafloxacin salts 1, of the formula

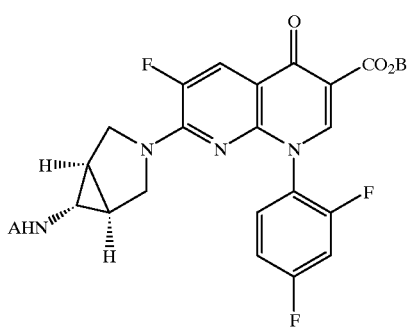

6 wherein A is hydrogen or an amine protecting group such as t-butyloxycarbonyl, benzyloxycarbonyl, ($C_1$–$C_6$) alkylcarbonyl and benzyl; and B is hydrogen or a carboxylic acid protecting group selected from benzyl, t-butyl and ($C_1$–$C_6$)alkyl; with an amine and/or carboxylic acid deprotecting agent, respectively.

A preferred compound 6, wherein A is hydrogen and B is ethyl, is converted to compound 2 by treatment with a solution of NaOH in a polar solvent at an elevated temperature. A preferred solvent is methanol and the temperature is the reflux temperature of the solvent. The pH of the solution was then adjusted to between about 6.5 and 8.0 with dilute HCl and saturated aqueous $NaHCO_3$ was then added to adjust the pH to between about 7.5 and 8.5. The product was recovered as indicated above.

Metastable trovafloxacin zwitterion 2 is converted to hygroscopic polymorph PII, 4, by treatment with a non polar solvent such as a hydrocarbon. A preferred hydrocarbon is hexanes. Residual water is removed azeotropically and the product dried at about 35 to about 40° C. under vacuum. Solvents useful for the azeotropic removal of water traces include non-polar aliphatic hydrocarbons, such as hexanes and octanes, and aromatic hydrocarbons such as benzene and toluene. Preferred solvents are the aliphatic hydrocarbons, most preferably hexanes.

Non hygroscopic polymorph PI 3, can be prepared from compound 2 by treatment with a polar solvent followed by azeotropic removal of water and vacuum drying at about 30 to about 40° C. Polar solvents useful for this conversion include ($C_1$–$C_6$)alkyl esters of ($C_2$–$C_6$)alkylcarboxylic acids and ($C_1$–$C_6$)alkanols. A preferred solvent is ethyl acetate.

Alternatively, compound 3 can be prepared from compound 4 by treating compound 4 with a refluxing polar solvent, as described above. A preferred solvent is is ethyl acetate.

Compound 5, the pentahydrate of the compound of formula I, is prepared by air drying the wet crystals of compound 1, at room temperature, until constant weight is achieved. Alternatively, compound 5 may be prepared from compound 4 by treatment with water until a constant water uptake has been obtained. Compound 3 is not converted to compound 5 by exposure to water.

The antibacterial compounds of the invention, i.e., polymorph PI, polymorph PII and the pentahydrate (hereafter "the active compounds") are useful in the treatment of animals and humans having a broad spectrum of bacterial infections. They are particularly useful in treating gram-positive bacterial strains.

The active compounds may be administered alone, but will generally be administered in a mixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously, For parenteral administration, they are best used in the form of a sterile aqueous solution which can contain other solutes, for example, enough salt or glucose to make the solution isotonic. In the case of animals, the compounds of formula I can be administered intramuscularly or subcutaneously at dosage levels of about 0.1 to about 50 mg/kg/day, advantageously about 0.2 to about 10 mg/kg/day given in a single daily dose or up to 3 divided doses.

The active compounds can be administered to humans, for the treatment of bacterial diseases by either oral or parenteral routes. They may be administered orally at dosage levels of about 0.1 to 500 mg/kg/day, advantageously 0.5–50 mg/kg/day given in a single dosage or up to 3 divided dosages. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The active compounds may be administered alone, but will generally be administered in a mixture with a pharmaceutical carrier selected with regard to the intended route of administration and standard pharmaceutical practice. For example, they can be administered orally or in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water in a concentration of about 5 to about 5000 ppm, preferably about 25 to about 500 ppm. They can be injected parenterally, for example, intramuscularly, intravenously or subcutaneously. For parenteral administration, they are best used in the form of a sterile aqueous solution which can contain other solutes, for example, enough salt or glucose to make the solution isotonic. In the case of animals, the compounds of formula I can be administered intramuscularly or subcutaneously at dosage levels of about 0.1 to about 50 mg/kg/day, advantageously about 0.2 to about 10 mg/kg/day given in a single daily dose or up to 3 divided doses. The active compounds can be administered to humans by either oral or parenteral routes, and may be administered orally at dosage levels of about 0.1 to 500 mg/kg/day, advantageously 0.5–50 mg/kg/day given In a single dosage or up to 3 divided dosages. For intramuscular or intravenous administration, dosage levels are about 0.1–200 mg/kg/day, advantageously 0.5–50 mg/kg/day. While intramuscular administration may be a single dose or up to 3 divided doses, intravenous administration can include a continuous drip. Variations will necessarily occur depending on the weight and condition of the subject being treated and the particular route of administration chosen as will be known to those skilled in the art.

The antibacterial activity of the compounds of the invention is shown by testing according to the Steer's replicator technique which is a standard in vitro bacterial testing method described by E. Steers et al., Antibiotics and Chemotherapy, 9, 307 (1959).

The following examples illustrate the methods and compounds of the present invention. It will be understood, however, that the invention is not limited to the specific examples.

EXAMPLE 1

Trovafloxacin Zwitterion, Metastable Form

A. Trovafloxacin mesylate (prepared according to Example 13B of the '402 patent) (20 g) was stirred with demineralized water (100 mL). The crystal slurry was heated to about 50° C. and the slurry adjusted to a pH of about 8.0 by addition of saturated sodium bicarbonate solution. The slurry was held at about 50° C. for 30 minutes, allowed to cool to about 25° C. and stirred at this temperature for 30 minutes. The crystals were isolated by filtration and washed with demineralized water (27 mL). The wet crystals were suspended in demineralized water (100 mL) and stirred for about 1 hour at about 50° C., then cooled to about 20° C. and stirred at this temperature for about 1 hour. The crystals were filtered from the mother liquor, washed with demineralized water (about 27 mL) and dried to constant weight under vacuum at about 40° C. to yield the title product which contained 2.5% residual water by analysis. Yield 16.25 g, 97%.

B. The ethyl ester of trovafloxacin (prepared according to the method of copending U.S. patent application Ser. No. 08/490827, filed Jun. 15, 1995, the disclosures of which are hereby incorporated herein by reference in its entirety. The foregoing application is assigned in common with the present application. (10 g) was stirred with methanol (75 mL), water (25 mL) and sodium hydroxide pellets (1.8 g). The resultant mixture was heated to reflux at about 72° C. to form a solution. The solution was cooled to about 25° C. and the pH adjusted to about 7.5, by addition of 6N hydrochloric acid, to form a slurry. Saturated sodium bicarbonate solution (50 mL) was added and the slurry stirred for 30 minutes at about 25° C. The title product was isolated and washed with water (20 mL) and dried under vacuum about 45° C. Yield 7.72 g, 82.5%.

EXAMPLE 2

Trovafloxacin Zwitterion Polymorph PI (non hygroscogic form)

Trovafloxacin mesylate, (75 g) was stirred with demineralised water (375 mL). The crystal slurry was heated to about 50° C. and the slurry adjusted to a pH of about 8.0 by addition of saturated sodium bicarbonate solution. The slurry was held at about 50° C. for 30 minutes, allowed to cool to about 25° C. and stirred at this temperature for 30 minutes. Crystals were isolated by filtration and washed with demineralised water (100 mL). The wet crystals were suspended in demineralised water (375 mL) and stirred for 1 hour at about 50° C., then cooled to about 20° C. and stirred at this temperature for about 1 hour. The crystalline product was filtered from the mother liquor and washed with demineralised water (about 100 mL). The wet crystals were stirred with ethyl acetate (1125 mL) and the resultant slurry heated to reflux and the water azeotropically removed. The essentially anhydrous slurry was cooled to about 25° C., the crystals were isolated by filtration and dried under vacuum at 40° C. until all the solvent had been removed to provide the title product. Yield 60.9 g, 94%.

The product is characterized by the X-ray powder diffraction pattern described above.

EXAMPLE 3

Trovafloxacin Zwitterion Hygroscopic Polymorph PII

The title product of Example 1, paragraph A, (5 g) was mixed with hexanes (150 mL) to form a slurry. The slurry was heated to reflux and traces of residual water were removed azeotropically. After 4 hours at reflux the crystal slurry was cooled to about 25° C., isolated by filtration and dried to constant weight under vacuum at about 40° C. Yield 4.7 g, 94%. The title product was characterized by the X-ray powder diffraction pattern described above.

EXAMPLE 4

Trovafloxacin Zwitterion Pentahydrate

Trovafloxacin mesylate (50 g) was stirred with demineralised water (250 mL). The crystal slurry was heated to 50° C. and the slurry adjusted to a pH of about 8.0 by addition of saturated sodium bicarbonate solution. The slurry was held at about 50 OC for 30 minutes, allowed to cool to about 25° C. and stirred at this temperature for 30 minutes. The crystals were isolated by filtration and washed with demineralised water (70 mL). The wet crystals were suspended in demineralised water (250 mL) and stirred for 1 hour at about 50° C., then cooled to about 20° C. and stirred at this temperature for about 1 hour. The crystalline product was filtered from the mother liquor, washed with demineralised water (about 70 mL). The wet crystals were air dried to constant weight at room temperature to yield the title product which contained 17.6% water by analysis. Yield 48.4 g, 84%

The title product was characterized by the X-ray powder diffraction pattern described above.

We claim:

1. A trovafloxacin zwitterionic crystal form having the formula

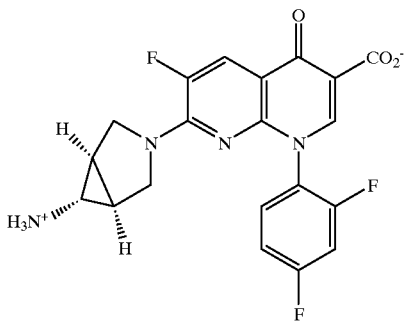

I which is a non hygroscopic first polymorph PI exhibiting the characteristic X-ray powder diffraction pattern

| Peak no. | 1 | 2 | 3 | 4 | 5 | 6 | 7 | 8 |
|---|---|---|---|---|---|---|---|---|
| $2\_\theta\_(°)$ Cu | 6.9 | 9.8 | 11.3 | 12.0 | 13.9 | 16.1 | 16.6 | 17.1 |
| d space | 12.7 | 9.0 | 7.9 | 7.4 | 6.4 | 5.5 | 5.4 | 5.2 |

| Peak no. | 9 | 10 | 11 | 12 | 13 | 14 | 15 |
|---|---|---|---|---|---|---|---|
| $2\_\theta\_(°)$ Cu | 17.4 | 19.7 | 20.3 | 21.2 | 22.8 | 23.8 | 26.3 |
| d space | 5.1 | 4.5 | 4.4 | 4.2 | 3.9 | 3.7 | 3.4. |

2. A process for preparing a compound of the formula

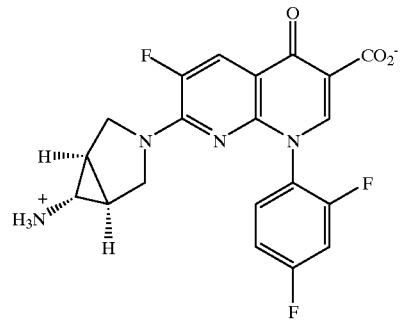

I which is the non hygroscopic polymorph PI, of claim 1, comprising

A. the steps of treating an aqueous suspension of a metastable form of the compound of the formula I 1) with a polar solvent followed by azeotropic removal of residual water and vacuum drying to form the non-hygroscopic first polymorph PI, or
2) with a nonpolar solvent followed by azeotropic removal of residual water and vacuum drying to form the hygroscopic polymorph PII which exhibits the following characteristic X-ray powder diffraction pattern:

| Peak no. | 1 | 2 | 3 | 4 | 5 | 6 | 7 | 8 |
|---|---|---|---|---|---|---|---|---|
| $2\_\theta\_(°)$ Cu | 8.4 | 9.5 | 10.2 | 14.7 | 16.8 | 17.9 | 22.6 | 26.1 |
| d space | 10.6 | 9.3 | 8.7 | 6.0 | 5.3 | 5.0 | 3.9 | 3.4 | and treating the hygroscopic polymorph PII with a refluxing polar solvent to form the non-hygroscopic polymorph PI.

3. The process of claim 2 wherein the metastable form, of the compound of formula I, is prepared by
a) treating an acid salt of trovafloxacin with a base to raise the pH of the mixture to between 7.5 and 8.5 at an elevated temperature; or
b) by treating a compound of the formula

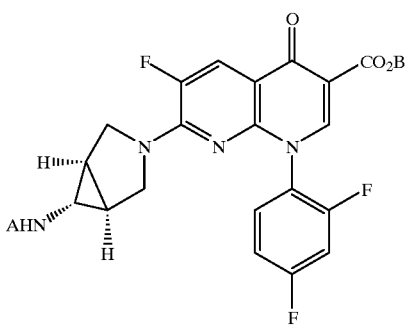

II wherein A is hydrogen or an amine protecting group selected from t-butyloxycarbonyl, benzyloxycarbonyl, $(C_1-C_6)$alkylcarbonyl and benzyl; and B is hydrogen or a carboxylic acid protecting group selected from benzyl, t-butyl and $(C_1-C_6)$alkyl; with an amine and/or carboxylic acid deprotecting agent, respectively.

4. The process of claim 2 step 2) wherein the non polar solvent is hexanes.

5. The process of claim 2 step 1) wherein the polar solvent is ethyl acetate.

6. A method for treating bacterial infection in a mammal which comprises administering to said mammal in need thereof a bacterial infection treating effective amount of the compound of claim 1.

7. A composition for treating bacterial infections in a mammal which comprises a bacterial infection treating effective amount of a compound of claim 1 and a pharmaceutically acceptable carrier.

8. The composition of claim 7 wherein said composition is a suspension.

* * * * *